(12) United States Patent
Hall et al.

(10) Patent No.: US 6,770,268 B1
(45) Date of Patent: Aug. 3, 2004

(54) NON-FOAMING ANTI-INFECTIVE PERIODONTIC COMPOSITIONS

(75) Inventors: Dave Hall, Auburn University, AL (US); James R. Hunt, Dunwoody, GA (US)

(73) Assignee: Oratec Corp., Manassas, VA (US)

( * ) Notice: Subject to any disclaimer, the term of this patent is extended or adjusted under 35 U.S.C. 154(b) by 0 days.

(21) Appl. No.: 10/442,621

(22) Filed: May 21, 2003

Related U.S. Application Data

(63) Continuation-in-part of application No. 10/141,232, filed on May 8, 2002, now Pat. No. 6,579,514.

(51) Int. Cl.$^7$ .................................................. A61K 7/22
(52) U.S. Cl. ........................ 424/54; 514/556; 514/900; 514/902; 514/944
(58) Field of Search ........................... 424/54; 514/556, 514/900, 902, 944

(56) References Cited

U.S. PATENT DOCUMENTS

| | | | | |
|---|---|---|---|---|
| 4,062,976 A | * | 12/1977 | Michaels | 424/319 |
| 4,130,637 A | * | 12/1978 | Bauman | 424/54 |
| 4,203,872 A | * | 5/1980 | Flanagan | 510/182 |
| 4,247,538 A | * | 1/1981 | Barker | 510/121 |
| 4,264,479 A | * | 4/1981 | Flanagan | 134/40 |
| 4,329,334 A | * | 5/1982 | Su et al. | 424/70.19 |
| 4,329,335 A | * | 5/1982 | Su et al. | 424/70.17 |
| 4,450,091 A | * | 5/1984 | Schmolka | 510/122 |
| 4,726,944 A | * | 2/1988 | Osipow et al. | 510/120 |
| 4,839,158 A | * | 6/1989 | Michaels | 424/54 |
| 5,225,112 A | * | 7/1993 | Miyazawa et al. | 510/124 |
| 5,244,652 A | * | 9/1993 | Michaels | 424/54 |
| 5,389,676 A | * | 2/1995 | Michaels | 514/556 |
| 5,679,324 A | * | 10/1997 | Hill et al. | 424/401 |
| 5,736,505 A | * | 4/1998 | Manzo et al. | 512/2 |
| 5,994,383 A | * | 11/1999 | Dyer et al. | 424/54 |
| 6,087,400 A | * | 7/2000 | Dyer et al. | 514/643 |
| 6,096,349 A | * | 8/2000 | Petri et al. | 424/616 |
| 6,096,702 A | * | 8/2000 | Ramirez et al. | 510/421 |
| 6,106,817 A | * | 8/2000 | Ramirez et al. | 424/70.19 |
| 6,579,514 B1 | * | 6/2003 | Hall et al. | 424/54 |

\* cited by examiner

*Primary Examiner*—Frederick Krass
(74) *Attorney, Agent, or Firm*—John Lezdey

(57) ABSTRACT

A non-foaming periodontic composition in a gel form or mouth wash for treating gum diseases or used in bleaching teeth which are alcohol free. The composition is a mixture of an isoalkyl amine oxide and an antimicrobial betaine compound. The composition is useful for treating gum disease and whitening teeth.

9 Claims, No Drawings

NON-FOAMING ANTI-INFECTIVE PERIODONTIC COMPOSITIONS

RELATED APPLICATION

This is a continuation-in-part of application Ser. No. 10/141,232 filed May 8, 2002 entitled, "Anti-Infective Periodontic Compositions" now U.S. Pat. No. 6,579,514.

FIELD OF THE INVENTION

The present invention relates to an improvement in periodontic compositions used in connection with tooth extractions and the treatment of gum diseases by dentists. More particularly, the present invention relates to a bleaching non-foaming gel antimicrobial periodontic composition, which contains a betaine compound and is free of alcohol, for use in the treatment of gum diseases, especially gingivitis and tooth whitening. Further, the compositions of the invention are incorporated in a mouth wash.

BACKGROUND OF THE INVENTION

It is desirable for uses in dentifices that a stable minimal or non-foaming gel be used in dentifices and in compositions used in treating gum diseases, it is advisable to provide a composition free of alcohols. Alcoholic compositions are considered as being potentially carcinogenic. The use of most gums or gels to improve the stability or foamability of the composition also dilutes the anti-microbial effect.

It is further desirable to provide a low foaming mouth wash having good detergency, tooth bleaching and high efficiency fragrance coupling.

A variety of microorganisms are also present in the oral cavity. These range from the natural flora of the host to pathogenic species. Among these microorganisms are the gram-positive rods associated with the formation of plaque (a dense, enamel adherent, microorganism-containing polysaccharide matrix). Even with good oral hygiene, it has been shown that microorganisms (including those responsible for plaque formation) rapidly build up in the oral cavity. Specific areas, including periodontal and subgingival spaces, and interpapillary spaces of the tongue present environments that harbor bateria. These species are difficult to reach by toothbrushing, and are only moderately affected by standard mouthwashes. The persistence of these microorganisms in such environments greatly increases, the risk of calculus and plaque build up and carie formation, which in turn presents the danger of gingival inflammation and periodontal disease.

Although mouthwashes are standard in oral hygiene, they have generally been used to mask halitosis. Several mouthwashes that have been marketed for the reduction of bacteria and the prevention of plaque buildup generally rely on a combination of alcohols (e.g. thymol, eucalyptol, ethanol; such as Listerine), a combination of alcohols and a quaternary amine (e.g. ethanol, cetylpyridinium chloride; such as Scope) or other oral surfactants (see U.S. Pat. No. 4,657,758), or of alcohol and chlorhexidine digluconate (Peridex from Proctor and Gamble). However, the use of alcohol containing formulations tends to produce unpleasant side effects including pain and stinging of the oral mucosa, foul aftertaste and discoloration of teeth. Prior art attempts to address this issue have included the use of a cetylpyridinium chloride in the presence of an oral surfactant (Lander Alcohol Free Mouthwash from the Lander Company, Inc.) and the use of stabilized chlorine (RetarDent from Rowpar). Because stabilized chlorine molecules are inactivated by interactions with proteins found in the mouth, they are unable to penetrate the occult, non-surface environments inhabited by microorganisms making these types of alcohol-free formulations of limited efficacy. In addition to this, these formulations sting open sores or cuts in the mouth.

U.S. Pat. No. 4,839,158 to Michaels, which is herein incorporated by reference discloses a dentifrice containing a betaine in an alcoholic composition containing gels, gums, and the like to form a foamable product. However, the addition of such foaming agents dilutes the anti-microbial effect of the composition and the foam produced is not stable for a sufficient length of time.

U.S. Pat. No. 5,389,676 to Michaels, which is herein incorporated by reference, discloses anti-infective water-in-oil or oil-in-water compositions comprising amphoteric surfactants of amine oxides, hydrophobic materials and emulsions aids, which can be used as a dentifrice. The compositions containing gelatins to improve Bloom strength and create a gel which results in a dilution of the antimicrobial effect.

U.S. Pat. Nos. 4,062,976, 4,127,328, 4,183,852, and 4,837,158 disclose amphoteric betaine and amine oxide foamable compositions but not those with a stable foam.

SUMMARY OF THE INVENTION

The present invention relates to an anti-infective, non-foaming periodontic gel compositions which is free from alcohols, which can be used in treating gum diseases, and whitening teeth. More particularly, there is provided a composition comprising an isoalkyl dimethyl amine oxide in combination with a betaine with a controlled foam which is free of clouding.

The composition contains about 0.1 to 10% mixture of the betaine and the isoalkyl dimethyl amine oxide in combination with optional fillers. Preferably, the composition comprises a ratio of about 1 to 2 betaine to an amine oxide compound of the formula:

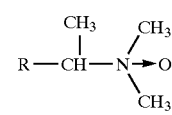

I wherein R is an aliphatic alkyl group of 7 to 14 carbon atoms.

Advantageously, the compositions of the invention can be incorporated into a dentifrice or a mouth wash.

It is therefore a general object of the invention to provide an anti-infective gel non-foaming periodontic composition having a broad spectrum of antimicrobial activity.

It is a further object of the invention to provide a non-foaming gel dentifrice which whitens teeth and is effective in treating gingivitis.

It is yet another object of the invention to provide a mouth wash composition to prevent staining of tooth enamel.

It is another object of the invention to provide a high detergency bleaching dentifrice and mouth wash.

It is a further object of the invention to treat a patient suffering from a gum disease with a dentifrice and/or a mouth wash.

DESCRIPTION OF THE PREFERRED EMBODIMENTS

In accordance with the invention there is provided an anti-infective non-foaming periodontic composition in the form of a dentifrice or mouth wash.

More particularly, there is provided a periodontic composition comprising about 0.1 to 10.0 weight percent of a mixture of a betaine and an so alkyl dimethylamine oxide wherein the betaine compound is in a ratio to the ethyloxylated tertiary amine of 1:3 to 5:1, preferably about 1:2. The non-foaming characteristics of the composition provides longer antimicrobial activity and improved adherence to the gums and teeth.

The iso-alkyldimethyl amine oxides of the invention have the general formula:

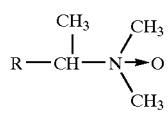

I wherein R is an alkyl group having 7 to 14 carbon atoms such as deca, undeca, dodeca, and trideca.

Suitable compounds include N,N-dimethy-1-(10-methyldecanamine oxide), which is also known as 10 methyldecyl-N,N-dimethylamine oxide, N,N-dimethyl-1-(11-methylundecanamine oxide), N,N-dimethyl-1-(12-methyldodecanamine oxide), N,N-dimethyl-1-(13-methyltridecanamine oxide), N,N-dimethyl-1-(14-methyltetradecanamine-oxide).

Illustrative of the betaine are: (1) coco-N-betaine, stearyl-N-betaine, isostearyl-N-betaine, oleyl-N-sulfobetaine; and (3) cocoamido-N-betaine, cetylamido-N-betaine, stearylamido-N-betaine, isostearylamido-N-betaine, oleyl-amino-N-betaine, and the like.

When used here the term "coco" is that used in the CTFA (designations of Cosmetic and Toiletry and Fragrance Association, Wash. D.C.) and is used to indicate alkyl groups present in coconut oil, i.e. a mixture of alkyl groups from 10 to 18 carbon atoms. The designations of the compounds listed herein are those of the CTFA.

Preferably, the betaines used in this invention are selected from the group consisting of (a) alkyl N-sulfobetaines, acyl-N-betaines, and mistures of two or more thereof. The term betaine when used herein means N-dimethyl glycine and its lower alkyl homologs. Unless otherwise specified an N-dimethyl compound is intended. The term sulfobetaine or sultaine means the sulfuric acid analog of such betaines.

Typically, the betaine and amine oxide components are present in molar ratios of from 1:3 to 5:1, preferably in a molar ratio of about 1:2. In general the acid necessary, when necessary to supply the required pH to the amphoteric surfactants can be any organic or inorganic acid, such as hydrochloric acid, phosphoric acid, sulfuric acid, citric acid, acetic acid, or nicotine acid. The operating pH for the surfactant composition is 4:8 to 7:8 preferably, from about 4:5 to 6:5. The pH of an aqueous solution comprising the above enumerated components is determined by employing an aqueous solution of 0.5% by weight, total of active components typically at a glass electrode, to precisely define the acidity.

For use in tooth extracted patients the composition can contain pain killers such as lidocaine, alphal-antitrypsin, or the like.

Hyaluronic acid acts both as a thickening agent and as a wound healer so that it is particularly preferred for use in tooth extractions.

If additional thickening agents are required, it is preferable to use carogeenan gum which is also antimicrobial or other natural antimicrobial gums. The additional fillers or ingredients can be used in an amount of about 0.1 to 10% by weight of composition.

The compositions are particularly useful in tooth extractions so as to heal without bacterial contamination from the mouth. The gel is useful especially in the treatment of gum disease and can be combined with conventional tooth paste.

The following examples illustrating the compositions of the invention are not intended to limit the scope of the invention.

EXAMPLE 1

A mixture of 1.210 Kg N,N-dimethyl-1-(11-methyl-undecanamine oxide) (i.e. Barlox 12i of Lonza Chemicals, Fair Lawn, N.J.) was mixed together with 0.575 Kg alcohol free Cetyl Betaine (Colateric BE16 from Colonial Chemicals, S. Pittsburgh, Tenn.) and Purified Water (USP) to give 10 Kg of mixture. The mixture was completely clear. A sample of the mixture was cooled to 0° C. and held for 24 hours. No cloudiness or separation of any of the ingredients was noted. Another sample was maintained at minus 10° C. for 24 hours. Upon thawing and agitation of the mixture, a clear solution was again obtained. The composition can be used as a mouthwash.

EXAMPLE 2

A mixture of the following was prepared.

1.30 Kg of the mixture from Example 1.
2.43 Kg Peppermint oil concentrate.
2.28 Kg Glycerin USP
15.25 g. Saccharin USP
7.6 g. Sodium Fluoride USP
Citric Acid (if required) to adjust pH to 4.7–4.9
38 Kg of Purified Water USP, q.s.

The mixture was clear both when freshly prepared above and after testing for separation and stability upon freezing as in example 1.

EXAMPLE 3

Tooth enamel was soaked in the solution prepared in example 2 for 24 hours. The tooth enamel was then subjected to coffee, tea, and cola solutions. No staining of the enamel was noted even after 24 hours exposure to the various solutions.

EXAMPLE 4

The various aerobic, anaerobic and facultative species shown in Table 1, were grown to maximum growth, i.e. about 5 days growth. The solution prepared in Example 1 was diluted 1 to 10, 1 to 100, 1 to 1000, and 1 to 10,000 using sterile saline as dileuents. Two mls of these dilutions were then added to 2 ml of Schaedler broth (a complex medium that supports the growth of most cultivable oral bacteria) in sterile test tubes. A further 1 to 2 dilutions to give final dilutions of 1 to 2, 1 to 20, etc., to the final dilutions shown in Table 1. No phosphate buffer was employed so as to prevent the phosphate ions binding with the cationic compounds. Each broth tube was then inoculated with 0.1 ml of the broth culture containing anaerobically in a chamber for 5 days after which the optical density was read at 600 nm. The results are given in Table 1. All strains were totally inhibited by the 1 to 20 dilutions.

TABLE 1

| Microorganism | Optical Density (600 nm at various dilutions) | | | | |
|---|---|---|---|---|---|
| | ½ | 1/20 | 1/200 | 1/2,000 | 1/20,000 |
| Anaerobic | | | | | |
| T. denticola | 0.0 | 0.0 | 0.42 | 0.8 | 0.49 |
| P. intermedia | 0.0 | 0.0 | 0.52 | 0.49 | 0.48 |
| P. gingivalis | 0.0 | 0.0 | 0.0 | 0.63 | 0.66 |
| Microaerophilic | | | | | |
| A.a | 0.0 | 0.0 | 0.64 | 0.74 | 0.76 |
| Facultative | | | | | |
| S. sanguis | 0.0 | 0.0 | 0.38 | 0.48 | 0.54 |
| S. mutans | 0.0 | 0.0 | 0.31 | 0.35 | — |
| A. viscosus | 0.0 | 0.0 | 0.93 | 0.91 | 0.95 |
| A. naeslundii | 0.0 | 0.0 | 0.93 | 0.97 | 0.96 |

EXAMPLE 5

The formulation in Example 1 was foamed in a foam generator and compared to the foam characteristics of the foams obtained when the amine oxide employed was decyl-N,N-dimethylamine oxide, lauryl-N,N-dimethylamine oxide, cetyl-N,N-dimethylamine oxide, oleyl N,N-dimentylamine oxide, stearyl N,N-dimethylamine oxide and myristamines. The foam generated employing the compound in example 1 gave virtually no stable foam compared to the other amine oxide combinations.

EXAMPLE 6

A formula was prepared by admixing the following:

| Ingredients | Parts by Weight |
|---|---|
| Lauryl Betaine | 100.0 |
| N,N-dimethyl-1-(11-methyl decanamine oxide) | 80.9 |
| Citric Acid monohydrate | 6.3 |
| Purified Water | 10.0 |

EXAMPLE 7

A gel composition can be prepared by admixing the following:

| Ingredients | Parts by Weight |
|---|---|
| N,N-dimethyl-1-(12-methyl dodecamine oxide) | 1.2 Kg |
| Cetyl Betaine | 0.6 Kg |
| Purified Water | q.s. 10 Kg |

Sufficient water was used to produce 10 Kg of mixture. The mixture formed a gel which can be used in the treatment of gingivitis.

EXAMPLE 8

A gel composition can be prepared by admixing the following:

| Ingredients | Parts by Weight |
|---|---|
| Cetyl Betaine | 35 g |
| Coco hydroxyl propyl solution | 37 g |
| Carageenan | 2 g |
| Citric acid monohydrate | 9 g |
| Purified Water | 10 g |
| N,N-dimethyl-1-(13-methyl tridecanamine oxide) | 76 g |

What is claimed is:

1. In an aqueous non-foaming, alcohol-free periodontic dentifrice composition containing an antimicrobial betaine, the improvement which comprises an effective amount of a tertiary amine oxide of the general formula:

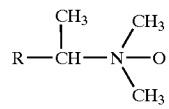

where R is an alkyl group having 7 to 14 carbon atoms, wherein a 1:20 saline dilution of said composition completely inhibits P. gingivalis growth in vitro for five days, as measured by optical density at 600 nm.

2. The composition of claim 1 wherein the betaine compound is in a ratio to the tertiary amine oxide of 1:3 to 5:1 and the composition bleaches teeth.

3. The composition of claim 1 wherein the composition has a pH between 4.8 and 7.8.

4. The composition of claim 1 wherein said betaine compound is selected from the group consisting of alkyl sultaine, alkyl amide ethyl betaine, alkyl, amine propyl betaine, alkyl-N-betaine, alkyl ethyl amide propyl hydroxyl sultaine, and alkyl hydroxyl propyl sultaine.

5. The composition of claim 4 wherein said betaine compound is selected from the group consisting of cetyl betaine and lauryl betaine.

6. The composition of claim 1 wherein said tertiary amine oxide is selected from the group consisting of N,N-dimethyl-1-(10-methyl-decanamine oxide), N,N-dimethyl-1-(11-methyl-undecanamine oxide), N,N-dimethyl-1-(12-methyl-dodecanamine oxide), N,N-dimethyl-1-(13-methyl-tridecanamine oxide), and N,N-dimethyl-1-(14-methyl-tetradecanamine-oxide).

7. The composition of claim 1 which is a gel.

8. The composition of claim 7 including a carageenan gum.

9. A method of treating a patient having gum disease and whitening teeth which comprises administering a therapeutically effective amount of the composition of claim 1 to a patient in need thereof.

* * * * *